United States Patent
Visscher et al.

(10) Patent No.: US 7,008,367 B2
(45) Date of Patent: Mar. 7, 2006

(54) ROW OF RADIOACTIVE SEEDS AND NON-RADIOACTIVE SPACERS AND CONNECTOR THEREFORE

(75) Inventors: Arie Luite Visscher, Driebergen (NL); Edgar German Loffler, Berlin (DE)

(73) Assignee: Nucletron B.V., Veenendaal (NL)

( * ) Notice: Subject to any disclaimer, the term of this patent is extended or adjusted under 35 U.S.C. 154(b) by 0 days.

(21) Appl. No.: 10/363,551

(22) PCT Filed: Sep. 3, 2001

(86) PCT No.: PCT/NL01/00647

§ 371 (c)(1),
(2), (4) Date: Mar. 5, 2003

(87) PCT Pub. No.: WO02/20089

PCT Pub. Date: Mar. 14, 2002

(65) Prior Publication Data

US 2004/0054249 A1 Mar. 18, 2004

(30) Foreign Application Priority Data

Sep. 5, 2000 (NL) .................................. 1016101

(51) Int. Cl.
*A61N 5/00* (2006.01)
(52) U.S. Cl. .......................................................... 600/8
(58) Field of Classification Search ................... 600/3, 600/7, 8, 585; 604/164.01, 249; 403/247, 403/252, 255, 264
See application file for complete search history.

(56) References Cited

U.S. PATENT DOCUMENTS

| | | | | |
|---|---|---|---|---|
| 4,697,575 A | * | 10/1987 | Horowitz | 600/8 |
| 4,784,116 A | * | 11/1988 | Russell et al. | 600/8 |
| 4,815,499 A | | 3/1989 | Johnson | |
| 5,713,828 A | * | 2/1998 | Coniglione | 600/7 |
| 5,738,663 A | * | 4/1998 | Lopez | 604/249 |
| 6,010,446 A | * | 1/2000 | Grimm | 600/3 |
| 6,200,258 B1 | * | 3/2001 | Slater et al. | 600/8 |
| 6,264,599 B1 | | 7/2001 | Slater et al. | |
| 6,273,851 B1 | | 8/2001 | Slater et al. | |
| 6,283,911 B1 | * | 9/2001 | Keren | 600/3 |
| 6,450,939 B1 | * | 9/2002 | Grimm | 600/8 |
| 6,497,647 B1 | * | 12/2002 | Tucker | 600/8 |
| 6,709,381 B1 | * | 3/2004 | Munro, III | 600/3 |

FOREIGN PATENT DOCUMENTS

| WO | WO 99/59675 A1 | 11/1999 |
|---|---|---|
| WO | WO 00/09211 A1 | 2/2000 |

* cited by examiner

Primary Examiner—John P. Lacyk
(74) Attorney, Agent, or Firm—Birch, Stewart, Kolasch & Birch, LLP

(57) ABSTRACT

An arranged row of radioactive seeds and non-radioactive spacers with a predetermined pitch can be provided with physical coherence by applying connectors between the separate seeds and spacers. In a first embodiment the connectors are elongated with introversions at both ends, in a second embodiment a connector also forms a spacer and is provided at one end with an introversion and at another end with a projection in the form of a seed.

8 Claims, 7 Drawing Sheets

ROW OF RADIOACTIVE SEEDS AND NON-RADIOACTIVE SPACERS AND CONNECTOR THEREFORE

This application is the national phase under 35 U.S.C. §371 of PCT International Application No. PCT/NL01/00647 which has an International filing date of Sept. 3, 2001, which designated the United States of America.

FIELD OF THE INVENTION

The invention relates to a row of radioactive seeds and non-radioactive spacers arranged with a predetermined pitch, in which the number of spacers can be zero, for a brachytherapeutic treatment of an animal body with radioactive radiation, which seeds have elongated shapes.

DESCRIPTION OF RELATED ART

Such a row is known from Dutch patent application 1012697 and American patent application Ser. No. 09/377,382.

Therein is disclosed a device for composing a row of radioactive seeds and non-radioactive spacers, in which the number of spacers can be zero, for a brachytherapeutic treatment of tissue with radioactive radiation. The seeds disclosed therein have an elongated shape. By means of the device disclosed in the above mentioned patent applications the row of radioactive seeds and non-radioactive spacers is entered into a hollow needle with an open end which open end has been temporarily closed with a plug of wax. After the row of radioactive seeds and non-radioactive spacers has been entered into the hollow needle the relevant needle is subsequently inserted in the body comprising the tissue to be irradiated. After the needle with the row of radioactive seeds and non-radioactive spacers has been entered into or near to the tissue to be irradiated a plunger causes the row of radioactive seeds and non-radioactive spacers to remain at its place and the hollow needle is retracted. By retracting the plug of wax is pushed against the row of radioactive seeds and non-radioactive spacers and subsequently the plug releases from the open end of the hollow needle. On further retraction of the hollow needle the complete row of radioactive seeds and non-radioactive spacers is placed in or near to the tissue to be irradiated. Finally, the hollow needle and the plunger are removed from the body. In this way it is achieved that the row of radioactive seeds and non-radioactive spacers with a predetermined pitch has been placed in the body.

The disclosed manner of inserting a row of radioactive seeds and non-radioactive spacers has a disadvantage in that after the row has been inserted into the body or near to the tissue to be irradiated there is no physical relation anymore between the inserted seeds and spacers other than through the tissue of the body. That may have as a consequence that upon movements of the body in which the row of radioactive seeds and non-radioactive spacers has been inserted the radioactive seeds and non-radioactive spacers may move through the body/the tissue to be irradiated and as a consequence of such movement irradiate other tissue. That may be disadvantageous for the therapeutic treatment since the distribution of radioactive seeds and non-radioactive spacers has been calculated with great accuracy in order to reach an optimal result in respect of the irradiation of the tissue to be irradiated. This is the more important because in general not one but a number or even a great number of rows of radioactive seeds and non-radioactive spacers each arranged with a predetermined pitch, is inserted in order to irradiate the tissue, often cancerous tissue and spare the urethra.

BRIEF SUMMARY OF THE INVENTION

In the context of the present invention, the term "spacer" is defined as an element which substantially has the same form and substantially the same dimensions as the seed, but, contrary to a seed, is not radioactive.

There is a need for rows of radioactive seeds and non-radioactive spacers, arranged with a predetermined pitch, in which the number of spacers can be zero, for brachytherapeutic treatment of tissue with radioactive radiation in which better care can be taken that the mutual spatial arrangements of radioactive seeds and non-radioactive spacers upon movement of the body cannot mutually change places after insertion of the row into the body.

This object is achieved according to the invention in that connectors are present between successive seeds, which connectors have substantially elongated shapes with two ends, in that at least one end of each connector is provided with an introversion in a longitudinal direction of the connector, in that the introversion has a shape complementary to the shape of a seed and in the longitudinal direction of the connector has a dimension which at most is equal to half the length of a seed.

Thereby it is achieved that the physical coherence is present between successive seeds of a row of radioactive seeds and non-radioactive spacers. The seeds have been coupled to each other "mechanically" in the form of a flexible "chain". Contrary to a normal chain the seeds and the connectors are not fixed together which on the one hand ensures a certain degree of flexibility and on the other hand is not necessary since the tissue to be irradiated and the body, respectively exercise sufficient pressure to cause the seeds to remain pressed into the introversions.

As such U.S. Pat. No. 4,815,449 discloses a row of radioactive seeds and non-radioactive spacers arranged with a predetermined pitch, in which the number of spacers can be zero, for a brachytherapeutic treatment of tissue with radioactive radiation, which seeds have elongated shapes. The relevant seeds and spacers are surrounded by elongated cylindrical elements one cross-end of which is provided with a projection and an other cross-end of which is provided with an introversion. The projections have shapes complementary to those of the introversions. Identical elements thus achieved can be connected together into a row of elements. The row of elements come into being in that way has a large degree of stiffness, that is, is not flexible, and is provided with a sharp tip at the end that is being driven into the body. In this way the elements connected together form a needle with a sharp tip. After insertion of the row of radioactive seeds and non-radioactive spacers, which are present in the elements of the needle thus formed, the relevant needle with the sharp tip remains in the body. A disadvantage thereof is that movements of the body and/or the tissue in which the row of radioactive seeds and non-radioactive spacers, engineered as a needle, has been inserted upon movements on the one hand can be hindered because the needle thus formed is not flexible, that is behaves as a stiff elongated element in the body and on the other side that one of the ends of that stiff element is provided with a sharp tip. Upon movements that sharp tip can easily cause damage to the tissue about the tip causing traumatic tissue reaction. A further disadvantage is that the material from which the cover of the seeds and spacers has been manufactured must be of sufficient stiffness to be able to form a stiff needle. That limits the choice of materials suited for this purpose.

International Patent Application WO 99/59675 discloses a "spacer" element for treating prostate cancer, using an implant of radioactive seeds. The "spacer" element according to WO 99/59675 has a generally cylindrical exterior form and comprises a central section and two cup-like end sections. It is configured in such a way that it fits within a conventional needle, which is loaded with an alternating succession of radioactive seeds and "spacer" elements (with the meaning of WO 99/59675), for subsequent positioning in the prostate. It should be noted that with the "spacer" element according to International Patent Application WO 99/59675 a different element, i.e. a connecting element between two seeds, is meant which differs from the above defined term "spacer" according to the present invention.

International Patent Application WO 00/09211 discloses radioactive seeds provided with "gripping" ends. Such an end fits in a cavity in a bio-absorbable "spacer" according to WO 00/09211. Subsequent seeds are linked together by means of 'spacers' according to WO 00/09211 before being loaded in an injection needle, so as to remain connected to each other. It should be noted that with the "spacer" element according to International Patent Application WO 00/09211 a different element is meant which differs from the above defined term "spacer" according to the present invention. The "spacers" according to WO 00/09211 can have different lengths.

The preferred embodiment of a row according to the invention is characterised in that seeds and spacers have identical form and measurements and in that each end of each connector is provided with an introversion in longitudinal direction of the connector and in that each introversion is shaped complementary to the shape of a seed and in a longitudinal direction of the connector has dimensions smaller than half the length of a seed.

Thereby it is achieved that the row can be composed alternately comprising a seed or spacer and a connector. The calculated and desired radiation pattern is achieved by distributing seeds and spacers along the row in the rate calculated and coupling the seeds and spacers by means of the connectors.

A further preferred embodiment of a row according to the invention is characterised in that one or more spacers comprise connectors one end of which is provided with an introversion and an other end of which is provided with a projection having a shape identical to the shape as from an end of a seed.

Thereby it is achieved that on composing an arranged row of radioactive seeds and non-radioactive spacers only one action will be necessary to add one non-radioactive spacer to an already existing row in which the last element of the row is provided with an introversion and that subsequently through adding of this particular spacer the row again ends with an introversion such that either again such a spacer can be fitted or a seed can be fitted.

The invention also relates to a connector for forming a row as disclosed hereinbefore.

A particular embodiment of a connector according to the invention is characterised in that cross-sectional dimensions of an introversion are fractionally smaller than cross-sectional dimensions of a seed, in that the connector is manufactured of somewhat flexible material and in that at least over part of the length of an introversion and going from the end at which the introversion is present a slit has been provided which in a direction perpendicular to a longitudinal direction of the connector stretches from the outside of the connector to the introversion.

Thereby it is achieved that a mechanical clamping takes place of a radioactive seed and a non-radioactive spacer, respectively, which have been put in the relevant introversion.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now further be described with reference to the accompanying drawings, which are given by way of illustration only, and thus are not limitative of the present invention, and in which.

DETAILED DESCRIPTION OF THE INVENTION

Figure 1:
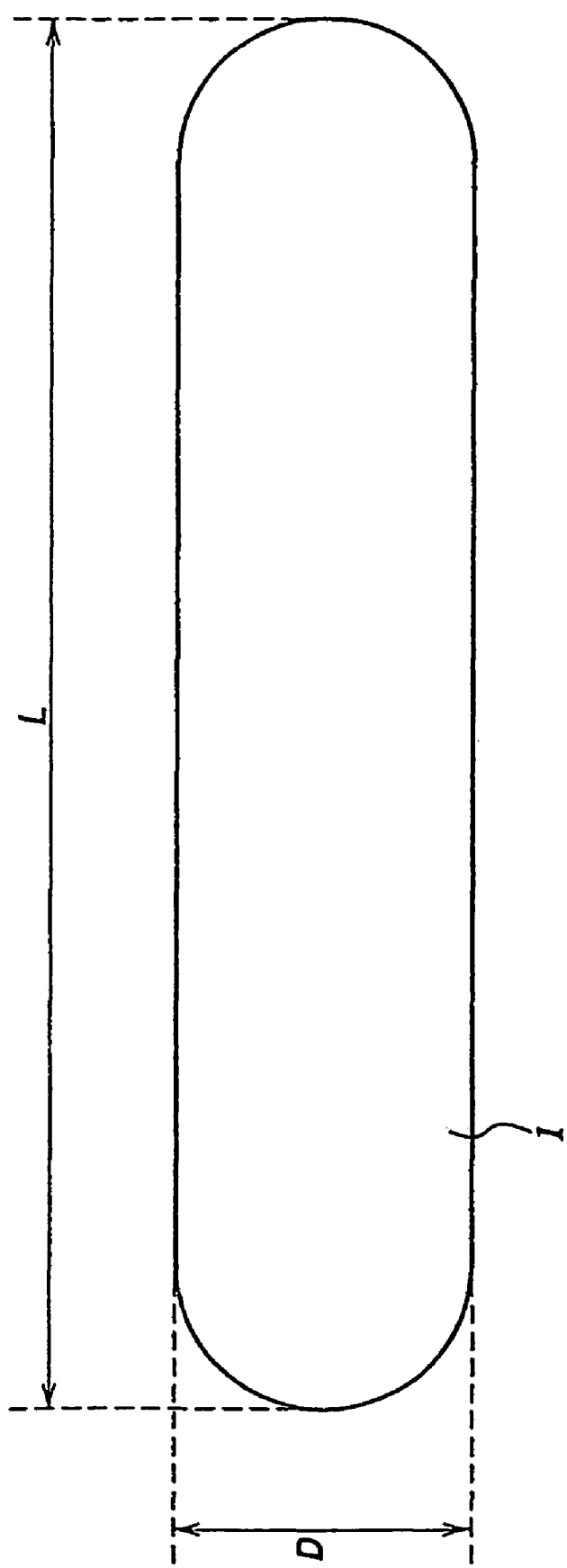
FIG. 1 shows, on an enlarged scale, a seed/spacer.
Figure 2:
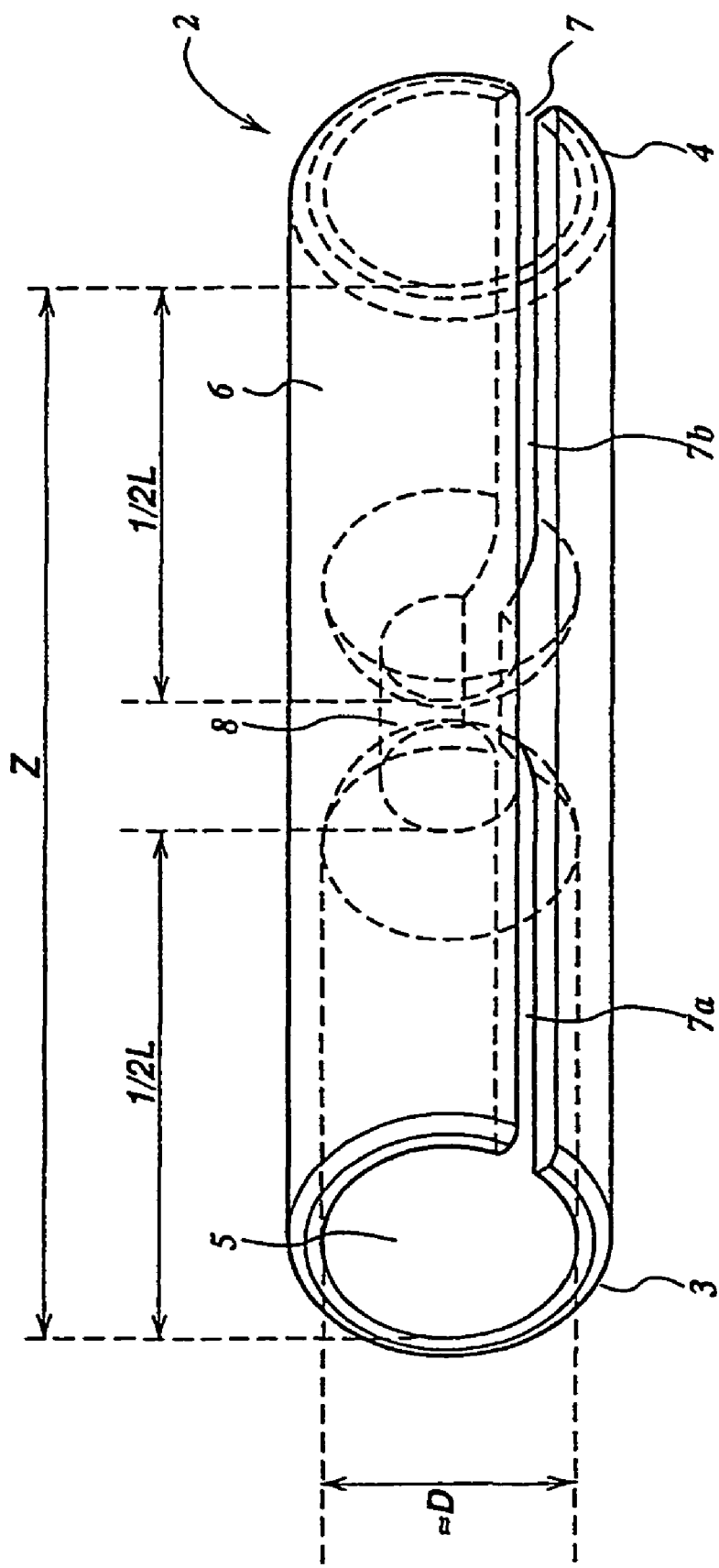
FIG. 2 shows a connector with introversions at both ends.
Figure 3:
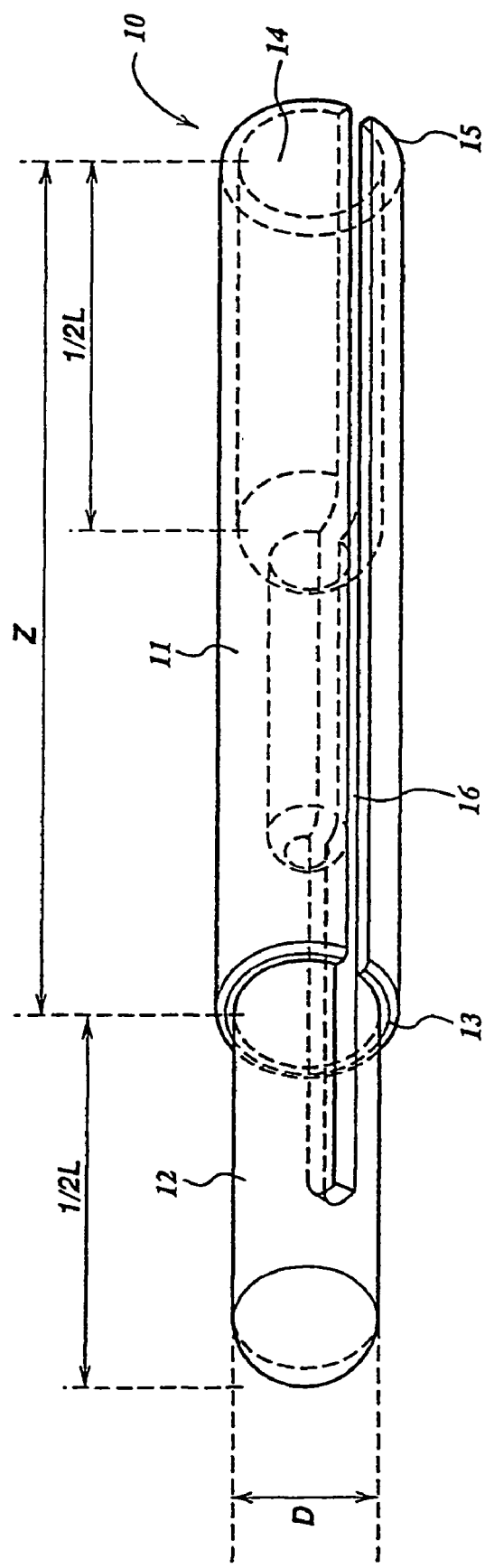
FIG. 3 shows a connector having an introversion at one end and having at an other end a shape identical to the shape of a seed.

Referring to FIG. 1 reference number 1 indicates the general shape of seeds. The seed has an elongated shape in which dimension L in longitudinal direction is of the order of 4,5 mm and in which the diameter D is of the order of 1 mm or smaller. In one embodiment of the invention the spacers are of the same dimensions as the seeds shown in FIG. 1. In another embodiment of the invention the spacers are shaped as shown in FIG. 3 to be discussed later on. In order to arrange seeds and spacers of the shapes and dimensions as shown in FIG. 1 into a row, such as described in the introduction, with a predetermined pitch, which row is physically coherent, connectors can be used such as shown in FIG. 2 with reference number 2. Connector 2 has been manufactured of bio-absorbable material, which in this field is an known group of materials. Element 2 has an elongated shape and is provided at both ends 3 and 4, respectively with introversions 5 and 6, respectively. Also element 2 of the embodiment shown in FIG. 2 has been provided all along its length with a slit 7. Element 2 is also provided with a connecting opening 8 between the introversions 5 and 6 and the slit 7 extends from the outside of the connector 2 to the introversions 5 and 6 and the connecting space 8 between said introversions. It is noted that the existence of the connecting space is optional as well as the slit 7 being continuous. Other embodiments of a connector 2 with introversions 5 and 6 at both ends 3 and 4 are made up by connecting space 8 not being present and/or by slit 7 not being continuous from end 3 to end 4. In the latter case the connector 2 comprises two slits at the location of the slit parts 7A and 7B of slit 7, which two slits are not connected together. The two slits mentioned in each case run from the outside of connector 2 to the introversions 5 and 6, respectively. Another embodiment of a connector 2 such as shown in FIG. 2 is made up by a connector in which no slit 7 is present at all.

In case connector 2 is provided with a continuous slit 7 or with two non-continuous slits at the location of the slit parts 7A and 7B the introversions 5 and 6 are somewhat flexible as a result of the presence of the slit and slits, respectively. In that case the diameter of the introversions 5 and 6 is fractionally smaller than the diameter D of a seed or a spacer. As a consequence, there is advantageously a slight degree of clamping which is favourable for the physical coherence of the row of radioactive seeds and non-radioactive spacers arranged with connectors 2. In the case of neither a continuous slit 7 nor two separate slits at the location of the slit parts 7A and 7B the shapes of the introversions 5 and 6 are not flexible. In that case the inner diameters of the introversions 5 and 6 should be fractionally larger than the diameter D of the radioactive seeds and non-radioactive spacers respectively, such as shown in FIG. 1 and/or in FIG. 3.

The choice to apply a slit 7 or two slits at the locations of the slit parts 7A and 7B is amongst others dependent upon the flexibility of the bio-absorbable material from which connector 2 has been manufactured. The stiffer the relevant material, the more need for slits 7.

The total length of connector 2 is indicated by Z. The lengths of introversions 5 and 6 are smaller than the length of a seed 1, preferably, but not necessarily, smaller than half the length of a seed 1. Preferably, but not necessarily, the lengths of the introversions 5 and 6 are equal. That has as an advantage that in composing an arranged row of radioactive seeds and non-radioactive spacers the orientation of the connector 2 in a row does not play a role. Logistically that produces advantages since in the processing of the connectors 2, such as in filling apparatus appropriate for composing an arranged row of radioactive seeds and non-radioactive spacers the orientation of the connector 2 does not have to be looked at.

In FIG. 1 a first embodiment of a spacer has been shown, namely that one having outer dimensions identical to the outer dimensions of a seed. FIG. 3 shows a second embodiment of a spacer. Spacer 10 shown in FIG. 3 comprises a part 11 having a length Z equal to the length Z of a connector 2 shown in FIG. 2. Further connector 10 comprises a projection 12 at the first end 13 and an introversion 14 at the second end 15 of the part 11. Projection 12 has the outer shape and dimensions of a part of a seed such as shown with reference number 1 in FIG. 1. The diameter of projection 12 is equal to the diameter D of a seed 1 and the length of projection 12 is smaller than or equal to half the length L of a seed 1. The length of introversion 14 is at most half the length L of a seed 1. The inner diameter of introversion 14 is substantially equal to the diameter D of the seed 1. Similarly to connector 2 connector 10 can be provided with a longitudinal slit 16 running from the outside of connector 10 to the inside of the introversion 14 and stretching along the length from the end 15 until at least part of the introversion 14. Slit 16 however can run amply into the projection 12 such as shown in the exemplary embodiment of connector 10 in FIG. 3. Similarly to connector 2 connector 10 is manufactured of bio-absorbable material; and amongst others the flexibility of the bio-absorbable material plays a role in the choice of applying a slit 16 of a certain length. In case a slit 16 is applied, the inner diameter of the introversion 14 is fractionally smaller than the diameter D of a seed 1 and a projection 12, respectively and in case no slit 16 is applied the inner diameter of the introversion 14 is fractionally larger than the diameter D of a seed 1 and a projection 12, respectively.

Figure 4:
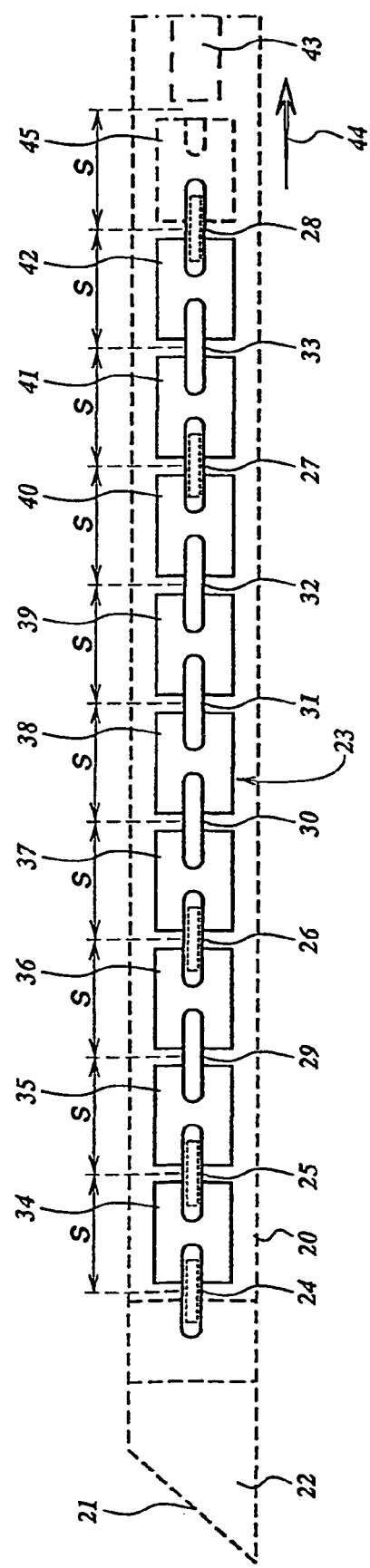
FIG. 4 shows a row of radioactive seeds and non-radioactive spacers with a predetermined pitch in a hollow needle with an open end, closed with a plug of wax.

FIG. 4 shows the way in which the physically coherent row of radioactive seeds and non-radioactive spacers arranged with the predetermined pitch can be put together by means of connectors 2 such as shown in FIG. 2. For distinction purposes seeds have been indicated in FIG. 4 as longitudinal shapes with a dashed rectangle inside while spacers have been indicated as longitudinal shapes only such as shown in FIG. 1. Reference number 20 schematically shows a hollow needle provided with an open end 21, which end has been shut with a plug of wax 22 in an known way. An arranged row of radioactive seeds 24, 25, 26, 27, and 28 with non-radioactive spacers 29, 30, 31, 32 and 33 between them has been shown in the hollow needle 20. The radioactive seeds and non-radioactive spacers are separated by connectors 34, 35, 36, 37, 38, 39, 40, 41 and 42. The connectors 34–42 are connected such as described in more detail in connection with FIG. 2. The connectors 34–42 take care of the desired physical coherence between the radioactive seeds and non-radioactive spacers of the arranged row 23. As a consequence of the identity of the longitudinal dimensions of the radioactive seeds and the non-radioactive spacers at a length Z of the connector 34–42 the arranged row 23 has a pitch S which is the same over the whole length of the arranged row 23. In connection with the pressing of the row 23 against the plunger, schematically shown with reference number 43, at the retraction of the needle 20 in the direction of the arrow 44 the end of the row 23 in touch with the plunger 43 can be made up of an extra connector 45.

Figure 5:
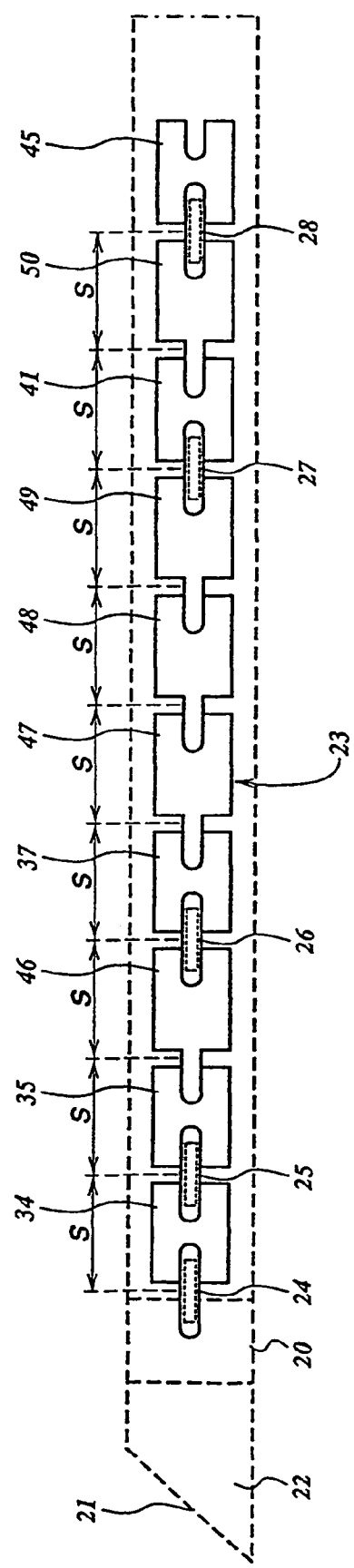
FIG. 5 shows a row of radioactive seeds and non-radioactive spacers arranged with a certain pitch according to another embodiment in a hollow needle an open end of which is closed with a plug of wax.

FIG. 5 again shows the same arranged row of radioactive seeds and non-radioactive spacers shown in FIG. 4 in which, however, in place of spacers according to the model shown in FIG. 1 use has been made of spacers according to the model shown in FIG. 3. Same elements as in FIG. 4 have been indicated with the same reference number. However, the combinations of spacers 29 with connector 36, spacer 30 with connector 38, spacer 31 with connector 39, spacer 32 with connector 40 and spacer 33 with connector 42 have been replaced by spacers 46 and 47 and 48 and 49 and 50, respectively. The number of elements to be pushed together in a row 23 according to FIG. 5, using spacers according to FIG. 3, is considerably smaller than the number of elements to be pushed together in making up an arranged row as shown in FIG. 4 with separate seeds, separate spacers and separate connectors.

Figure 6:
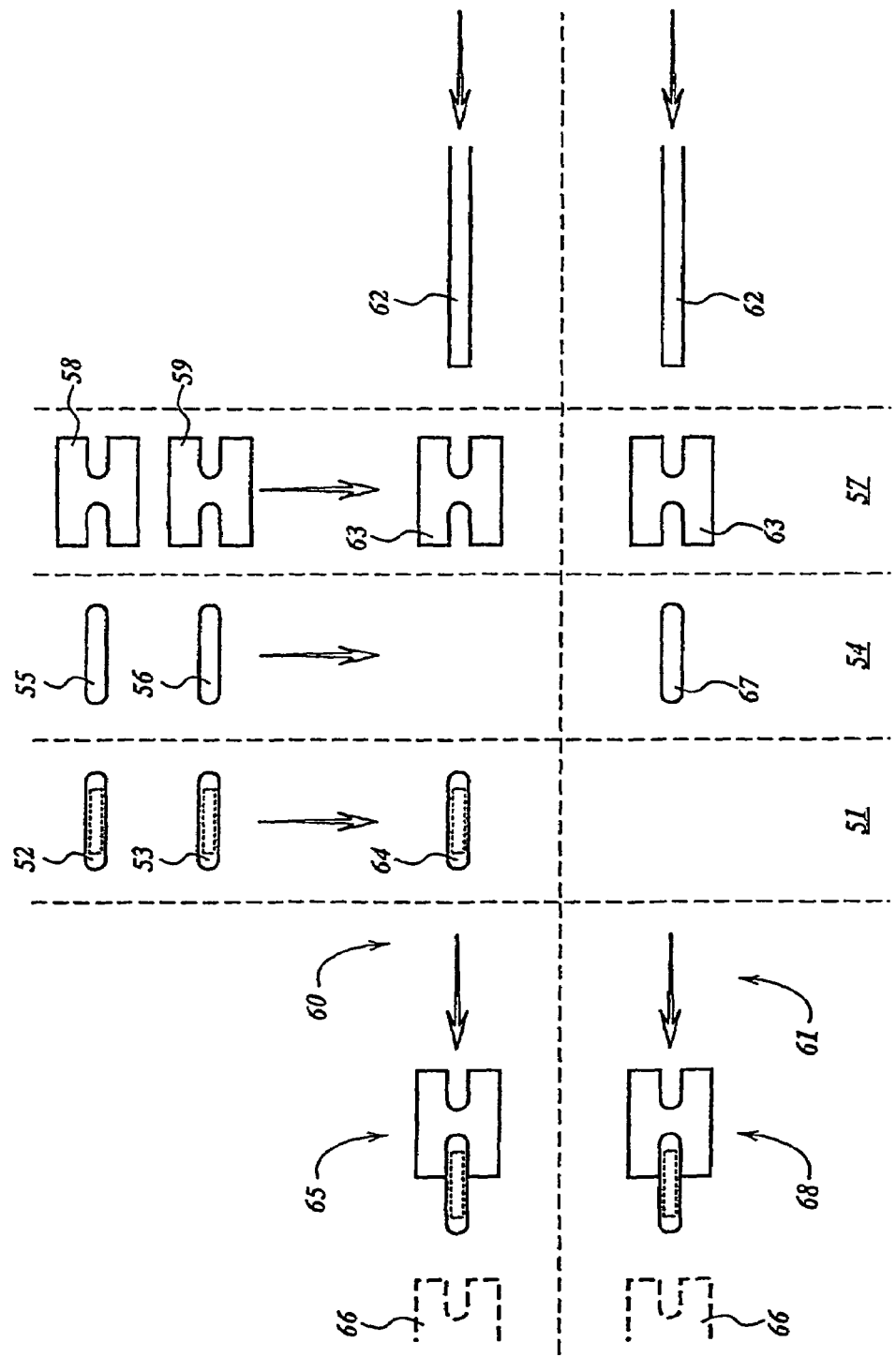
FIG. 6 shows schematically how a row of radioactive seeds and non-radioactive spacers can be put together with connectors according to FIG. 2.
Figure 7:
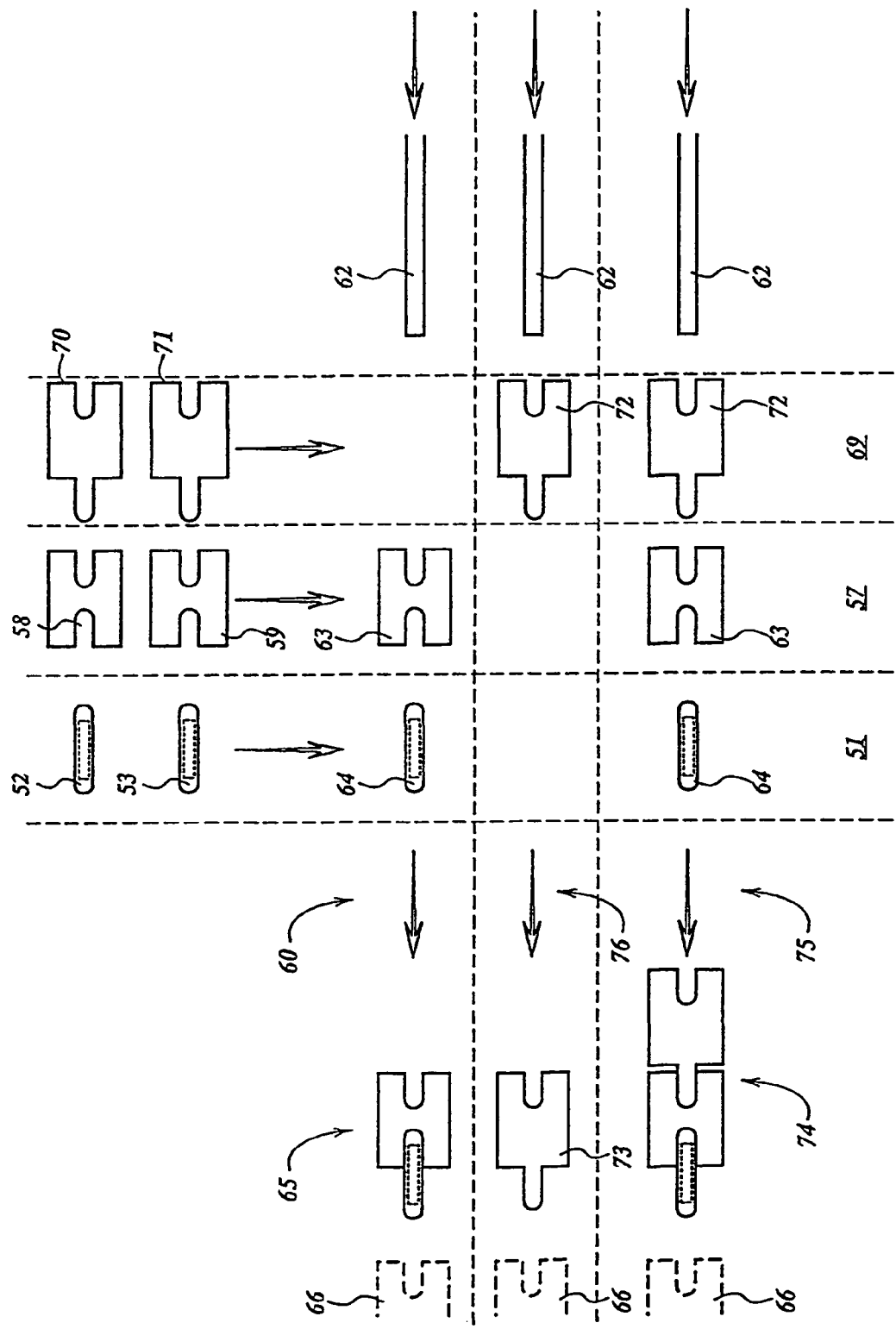
FIG. 7 shows how a row of radioactive seeds and non-radioactive spacers can be put together by means of connectors according to FIGS. 2 and 3.

FIGS. 6 and 7 show schematically in which way, starting from a store with radioactive seeds, a store with connectors and a store with spacers an arranged row of radioactive seeds and non-radioactive spacers can be put together. In FIG. 6 one starts with radioactive seeds and non-radioactive spacers according to the model shown in FIG. 1 and connector shown in FIG. 2. In FIG. 7 one starts with radioactive seeds according to the model shown in FIG. 1, spacers according to the model shown in FIG. 3 and connectors according to the model of shown in FIG. 2.

FIG. 6 shows three stores, a store 51 with schematically shown therein a number of seeds 52 and 53, a store 54 with shown schematically therein a number of spacers 55 and 56 and a store 57 with shown schematically therein an number of connectors 58 and 59, according to the model shown in FIG. 2. The stores 51, 54 and 57 have been provided with means to transport the radioactive seeds, non-radioactive spacers and connectors, respectively therein in the direction of a position in which an arranged row of the relevant seeds and spacers can be made up. For example, a device can be used such as disclosed in more detail in Dutch patent application 1012697 and U.S. patent application Ser. No. 09/377,382, respectively the contents of which applications are incorporated herein by reference. Each time a radioactive seed or a non-radioactive spacer has to be added to an already existing row of radioactive seeds and non-radioactive spacers, respectively each time a radioactive seeds is to form the first element of such row a radioactive seed and a non-radioactive spacer, respectively are transported from store 51 and store 54, respectively to a location where a putting together can take place of the relevant radioactive seed and the non-radioactive spacer, respectively with a connector according to the model disclosed in connection with FIG. 2 from the store 57. Reference number 60 indicates that by means of a plunger 62 a connector 63 and a radioactive seed 64 are linked up to a whole 65. The radioactive seed 64 either is the first element in an arranged row of radioactive seeds and non-radioactive spacers or is added to an already existing arranged row. In the latter case the radioactive seed 64 is pushed by the plunger 62 into an introversion of a previous connector at the end of the row mentioned, schematically indicated with the reference number 66.

Reference numeral 61 refers to the same course of things sketched in relation to the adding of a spacer 67 to an already existing row, the last connector of which has been indicated by reference numeral 66. Similarly to the description hereinbefore relating to a radioactive seed 64 the movement of a plunger 62 links up a connector 63 to a non-radioactive spacer 67 to a unit 68 which is brought into connection with the element 66 by the plunger 62.

In FIG. 7 elements already designated in FIG. 6 have been shown with the same reference numerals as used in FIG. 6. Store 54 with spacers 55 and 56 of the same shape and dimensions as the radioactive seeds is not present in FIG. 7 while a store 69 is present with a supply of spacers 70 and 71 according to the model of FIG. 3. Reference number 60 similarly to FIG. 6 shows linking up of a connector 63 according to the model shown in FIG. 2 with a radioactive seed 64 to a unit 65 which may form the forward end of an arranged row or may be added to an already existing arranged row the last element of which is shown in dashed lines with reference numeral 66. Reference number 75 shows how a combination of a radioactive seed 66, a connector 63 recording to the model shown in FIG. 2 and a spacer 72 according to the model shown in FIG. 3 can be linked up in one stroke and can form the beginning of a newly to be formed row or can be added to an already existing row the last element of which is a connector according to FIG. 2 or a spacer according to FIG. 3 and in which the radioactive element can be pushed into the introversion 77 thereof. On putting together a unit 74 comprising a radioactive seed 64, a connector 63 according to the model shown in FIG. 2 and a spacer 72 according to the model shown in FIG. 3 an element is transported from each of the stores 51, 57 and 69 to a trajectory of the plunger 62. Subsequently the plunger 62 is operated to press the elements 64, 63 and 72 together to an element 74.

Reference numeral 76 indicates which actions are taken when two or more subsequent spacers of the model shown in FIG. 3 have to form part of an arranged row of radioactive seeds and non-radioactive spacers. In that case for each spacer to be added to an already existing row a spacer 72 is transported in the trajectory of the plunger 62, which spacer 72 subsequently forms an element 73 that is being coupled to an already existing end 72' of a previous spacer of the same model.

After the foregoing many possibilities for executing the invention will be obvious for the person skilled in the art. All these embodiments are considered to embody the invention which has been put under protection according to the accompanying claims.

What is claimed is:

1. A row of radioactive seeds and non-radioactive spacers arranged with a predetermined pitch, in which the number of non-radioactive spacers can be equal to one or more, for a brachytherapeutic treatment of an animal body with radioactive radiation, which seeds and spacers have elongated shapes, the row being composed by alternately comprising a seed or a spacer and a connector, the seeds and the spacers being coupled by the connectors, which connectors have substantially elongated shapes with two ends, at least one end of each connector being provided with an introversion in a longitudinal direction of the connector, the introversion having a shape complementary to the shape of the seed and in the longitudinal direction of the connector has a dimension which is less than the length of the seed.

2. The row according to claim 1, wherein the seeds and spacers have identical shapes and dimensions and that each end of each connector is provided with an introversion in longitudinal direction of the connector and in that each introversion has a shape that is complementary to the shape of the seed and in the longitudinal direction of the connector has a dimension smaller than the length of the seed.

3. The row according to claim 1, wherein one or more spacers comprise connectors, one end of which is provided with the introversion and another end of which is provided with a projection having a shape identical to the shape as from an end of the seed.

4. The row according to claim 3, wherein the length of the projection is smaller than half a length of the seed.

5. The row according to claim 1, wherein a dimension of the introversion in the longitudinal direction of the connector is at most equal to half of the length of the seed.

6. A connector for putting together a row of radioactive seeds and non-radioactive spacers arranged with a predetermined pitch, in which row the number of non-radioactive spacers can be equal to one or more, for a brachytherapeutic treatment of an animal body with radioactive radiation, which seeds and spacers have elongated shapes, the connector having an introversion at each end extending in a longitudinal direction of the connector, each introversion having a shape that is complimentary to a shape of a seed or a spacer, the connector having a length at least being equal to a length of the seed or the spacer and wherein the length of each introversion is equal to half a length of the seed or the spacer.

7. The connector according to claim 6, wherein between both introversions seen in longitudinal direction no connection space is present.

8. A connector for putting together a row of radioactive seeds and non-radioactive spacers arranged with a predetermined pitch, in which row the number of non-radioactive spacers can be equal to one or more, for a brachytherapeutic treatment of an animal body with radioactive radiation, which seeds and spacers have elongated shapes, the connector having one end provided with an introversion and another end of the connector being provided with a projection, having a shape identical to an end of a seed.

* * * * *